United States Patent [19]

Lewis

[11] Patent Number: 4,814,541

[45] Date of Patent: Mar. 21, 1989

[54] CHEMICAL CONVERSION PROCESS

[75] Inventor: Jeffrey M. O. Lewis, Charleston, W. Va.

[73] Assignee: UOP, Des Plains, Ill.

[21] Appl. No.: 70,579

[22] Filed: Jul. 7, 1987

[51] Int. Cl.⁴ ................................................ C07C 1/00
[52] U.S. Cl. .................................... 585/640; 585/733
[58] Field of Search ................................ 585/640, 733

[56] References Cited

U.S. PATENT DOCUMENTS

| | | | |
|---|---|---|---|
| 3,861,005 | 1/1975 | Steinmetz et al. | 585/739 |
| 3,888,896 | 6/1975 | Espino et al. | 260/449.5 |
| 4,031,123 | 6/1977 | Espino et al. | 260/449.5 |
| 4,423,265 | 12/1983 | Chu et al. | 585/469 |
| 4,429,177 | 1/1984 | Morganson et al. | 585/525 |
| 4,440,871 | 3/1984 | Lok et al. | 502/214 |
| 4,499,327 | 2/1985 | Kaiser | 585/640 |
| 4,686,313 | 8/1987 | Bell et al. | 585/640 |

*Primary Examiner*—Curtis R. Davis
*Attorney, Agent, or Firm*—Gerald L. Coon

[57] ABSTRACT

A process for catalytically converting a feedstock into a product comprising contacting the feedstock with crystalline microporous three dimensional solid catalyst having the ability to promote the conversion at conditions effective to convert the feedstock to the product, the solid catalyst being present in a slurry with a liquid other than the feedstock or the product which is less reactive than the feedstock.

48 Claims, No Drawings

CHEMICAL CONVERSION PROCESS

FIELD OF THE INVENTION

This invention relates to a chemical conversion process employing a catalyst. More particularly, the invention relates to such a chemical conversion process employing certain defined catalysts and reaction systems which provides outstanding results.

BACKGROUND OF THE INVENTION

Chemical conversions employing solid catalysts are often conducted using a fixed or fluidized bed of catalyst particles. That is, the material to be converted is contacted with a solid catalyst present in a fixed bed of particles or in a fluidized bed of particles. however, each of these two modes of operation has serious disadvantages. For example, the use of a fixed catalyst bed often results in temperature control problems which adversely affect catalyst performance. Regeneration and/or reactivation of a fixed catalyst bed can result in substantial process downtime since the chemical conversion must be stopped in order to treat the catalyst, e.g., while the catalyst remains in the reactor vessel. Obtaining a uniform catalyst activity distribution is also difficult with fixed catalyst beds, in particular in situations where frequent regenerations are required.

Fluidized catalyst beds do, in general, provide better temperature control than do fixed catalyst beds. However, fluidized catalyst bed reaction systems are also much more complex than fixed catalyst bed reaction systems. For example, fluidized catalyst bed reaction systems usually involve at least two separate vessels each containing a fluidized catalyst bed, one in which to conduct the chemical conversion and one in which to regenerate and/or reactivate the catalyst. Catalyst particles are transferred, e.g., substantially continuously transferred, between the two separate vessels. Separation devices, e.g., cyclone separators and slide valve assemblies, are often needed to separate the catalyst particles from the feedstock/reaction product and the regeneration/reactivation medium and to control the flow of catalyst between the two vessels. Also, the catalyst particles, although relatively small to permit fluidization, must be blended to include added components, such as binders and often fillers, to strengthen the particles, e.g., against attrition, so that the particles can better withstand the constant and sometimes rather turbulent motion in the fluidized catalyst bed reaction system and separation devices. These added components, which are also often present in fixed bed catalysts as well, often promote undesirable chemical reactions or otherwise detrimentally affect the catalytic performance of the catalyst. Also, these added components may be particularly troublesome when used in conjunction with crystalline microporous three dimensional solid catalysts or CMSCs, i.e., catalysts which promote chemical reactions of molecules having selected sizes, shapes or transition states.

One alternative chemical reaction system involves the use of a catalyst slurry. In "Heterogeneous Catalyst in Practice" by Charles N. Satterfield, McGraw-Hill Book Company, New York (1980), at page 317 it is stated:

"The reaction of a liquid is often carried out by suspending a solid catalyst in a finely divided form in the liquid. This is often termed a slurry reactor'. If a gas is to be reacted with a liquid, it may be introduced through a distributor in the bottom of the vessel or it may be dispersed into the liquid by a mechanical agitator. This also acts to keep the solid suspended."

Thus, "slurry reactor" in the prior art is used to carry out a reaction of a liquid or of a gas and a liquid in the presence of a catalyst. For example, the Phillips Petroleum Company process for producing high density polypropylene utilizes slurry reactors. A fair amount of research effort has been directed to the use of slurry reactors, e.g., for making methanol from synthesis gas and for application to the Fisher-Tropsch reaction. See, for example, M. B. Sherwin, et al, "Make Methanol by Three Phase Reaction", Hydrocarbon Processing, p. 122–124, November, 1976; U.S. Pat. Nos. 3,888,896 and 4,031,123; M. L. Riekena, et al, "A Comparison of Fisher-Tropsch Reactors", Chemical Engineering Progress, p. 86–90, April, 1982; C. N. Satterfield, et al, "Usefulness of a Slurry Type Fishcher-Tropsch Reactor for Processing Synthesis Gas of Low Hydrogen-Carbon Monoxide Reactors", Canadian Journal of Chemical Engineering, Vol. 60, p. 159–162, 1982.

Slurry reaction system do provide substantial benefits. For example, temperature control is relatively easily maintained in such systems. However, selectivity to desired products may suffer because of relatively prolonged contacting between the catalyst and liquid reactant and product. It would be advantageous to provide a new chemical conversion process employing a solid catalyst.

Methanol is readily producible from coal and other raw materials by the use of well-known commercial processes. For example, synthesis gas can be obtained by the combustion of any carbonaceous material including coal or any organic material such as hydrocarbons, carbohydrates and the like. The synthesis gas can be manufactured into methanol by a well known heterogeneous catalytic reaction.

"Hydrocarbons from Methanol" by Clarence D. Chang, published by Marcel Dekker, Inc. N.Y. (1983) presents a survey and summary of the technology described by its title. Chang discusses methanol to olefin conversion in the presence of molecular sieves at pages 21–26. The examples given by Chang as suitable molecular sieves for converting methanol to olefins are chabazite, erionite, and synthetic zeolite ZK-5.

Catalysts comprising one or more crystalline microporous three dimensional materials or CMSMs include naturally occurring molecular sieves and synthetic molecular sieves, together referred to as "molecular sieves," and layered clays.

Among the CMSMs that can be used to promote converting methanol to olefins are non-zeolitic molecular sieves or NZMSs, such as aluminophosphates or ALPOs, in particular silicoaluminophosphates or SAPOs disclosed in U.S. Pat. No. 4,440,871. U.S. Pat. No. 4,499,327, issued Feb. 12, 1985, discloses processes for catalytically converting methanol to light olefins using SAPOs at effective process conditions. Each of these U.S. Patents is incorporated in its entirety by reference herein. Also, see commonly assigned U.S. Patent Applications, Ser. Nos. 070,574, 070,575 and 070,578, all filed on an even date herewith. Each of these applications is incorporated in its entirety by reference herein.

SUMMARY OF THE INVENTION

A process for catalytically converting a feedstock into a product has been discovered. In one broad aspect, the present process comprises contacting the feedstock with a crystalline microporous three dimensional solid catalyst, a CMSC, having the ability to promote this conversion at conditions effective to convert the feedstock to the product, the catalyst being present in a slurry with a liquid other than the feedstock or the product which is less reactive than the feedstock.

DISCUSSION OF THE INVENTION

The present catalytic conversion process provides substantial benefits. For example, the use of a less reactive liquid in a slurry with the CMSC may improve overall process performance, e.g., effective temperature control and catalytic selectivity to the desired product.

The process according to the invention provides improved temperature control for several reasons. The transfer of heat between a solid surface such as the catalyst and a liquid such as the suspending liquid is much better than the transfer of heat between such a solid and a gas as in the case of many fixed catalyst bed and fluidized catalyst bed prior art processes. The rate of heat transfer between the suspending liquid and the reaction zone wall is also enhanced and this allows better control of the temperature of the reaction zone contents. In the event of a possible overheating, the suspending liquid could boil and thus limit the extent of any thermal runaway. Additionally, the possibility of hot spots which can damage a catalyst in a fixed catalyst bed system is unlikely to occur in the instant process due to the slurry.

The slurry environment of the present process allows for effective control of the activity of the catalyst and reduces much of the physical and mechanical wear and tear on the solid catalyst. The composition of the catalyst particles can be adjusted to improve catalytic performance without incurring substantial physical losses of catalyst. The present slurry reaction system lends itself to other modifications or applications, e.g., as described herein, which result in improved process performance. Also, the present chemical conversion system can be relatively easily scaled up to a commercial sized unit based on data from a relatively small, pilot plant.

In short, the present process is an effective approach for chemical conversion which takes advantage, preferably increased advantage, of MCSCs.

As noted above, CMSCs are catalysts which promote chemical reactions of molecules having selected sizes, shapes or transition states. That is, CMSCs are catalysts which promote chemical reactions of feedstock molecules which conform to a given molecular size, molecular shape or transition stage constraint. Different CMSCs have different size/shape/transition stage constraints depending on the physical structure and chemical composition, for example, the effective diameter of the pores, of the catalyst. Thus, the particular CMSC chosen for use depends on the particular feedstock employed, and the particular chemical (reaction) and product desired. Preferably, the CMSC has a substantially uniform pore structure, e.g., substantially uniformly sized and shaped pores. CMSCs include, for example, layered clays; zeolitic molecular sieves and non-zeolitic molecular sieves or NZMSs.

The presently useful NZMSs include molecular sieves embraced by an empirical chemical composition, on an anhydrous basis, expressed by the formula:

$$mR:(Q_wAl_xP_ySi_z)O_2 \qquad (I)$$

where "Q" represents at least one element present as a framework oxide unit "$QO_2^n$" with charge "n" where "n" : may be $-3$, $-2$, $-1$, 0 or $+1$; "R" prepresents at least one organic templating agent present on the intracrystalline pore system; "m" represents the molar amount of "R" present per mole of $(Q_wAl_xP_ySi_z)O_2$ and has a value from zero to about 0.3; and "w", "x", "y" and "z" represent the mole fractions of $QO_2^n$, $AlO_2^-$; $PO_2^+$, $SiO_2$, respectively, present as framework oxide units. "Q" is characterized as an element having a mean "T-O" distance in tetrahedral oxide structures between about 1.51 Å and about 2.06 Å. "Q" has a cation electronegativity between about 125 kcal/g-atom to about 310 kcal/gm-atom and "Q" is capable of forming stable Q-O-P, Q-O-Al or Q-O-Q bonds in crystalline three dimensional oxide structures having a "Q-O" bond dissociation energy greater than about 59 kcal/g-atom at 298° K.[1]; and "w", "x", "y" and "z" represent the mole fractions of "Q", aluminum, phosphorus and silicon, respectively, present as framework oxides said mole fractions being within the limiting compositional values or points as follows:

w is equal to 0 to 99 mole percent;
y is equal to 1 to 99 mole percent;
x is equal to 1 to 99 mole percent; and
z is equal to 0 to 99 mole percent.

[1] See the discussion at pages 8a, 8b and 8c of EPC Publication 0 159 624, published Oct. 30, 1985, about the characterization of "EL" and "M". Such are equivalent to Q as used herein.

The "Q" of the "QAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. Combinations of the elements are contemplated as representing Q, and to the extent such combinations are present in the structure of a QAPSO they may be present in molar fractions of the Q component in the range of 1 to 99 percent thereof. It should be noted that formula (I) contemplates the non-existence of Q and Si. In such case, the operative structure is that of aluminophosphate or $AlPO_4$. Where z has a positive value, then the operative structure is that of silicoaluminophosphate or SAPO. Thus, the term QAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various compositions and structures described in the patents and patent applications set forth in Table A, which follows, and by Flanigen et al., in the paper entitled, "Aluminophosphate Molecular Sieves and the Periodic Table," published in the "New Developments and Zeolite Science Technology" Proceedings of the 7th International Zeolite Conference, edited by Y. Murakami, A. Sijima and J. W. Ward, pages 103-112 (1986):

TABLE A

Subject Matter of Patent or Patent Application

Patent or Pat. Applic. No.: U.S. Pat. 4,567,029

MAPO's are crystalline metal aluminophosphates having a three-dimensional microporous framework structure of $MO_2^{-2}$, $AlO_2^-$ and $PO_2^+$ tetrahedral units and having an empirical chemical composition on an anhydrous basis expressed by the formula $mR:(M_xAl_yP_z)O_2$; where R represents at least one organic templating agent present in the intracrystalline pore system; m has a typical value of from 0 to 0.3 and represents the moles of R present per mole of $(m_xal_yP_z)O_2$; M represents magnesium, manganese, zinc or cobalt, x, y and z represent the mole fractions of M, aluminum and phosphorus, respectively, present as tetrahedral oxides. The fractions are such that they are within a tetragonal compositional area defined by points ABC and D of FIG. 1 of the drawings of the patent.

This patent, at column 6, describes the use of aluminophosphates as a source of phosphorus (lines 26-28) and as a source of aluminum (lines 38-40), and the use of seed crystals to aid in the crystallization of the desired molecular sieve (lines 59-63). Example 85 depicts the use of MAPO-36 as a seed for making MnAPO-36. The chemical composition of the MnAPO-36 fails to reveal the presence of any magnesium.

U.S. Pat No. 4,440,871

SAPO molecular sieves are a general class of microporous crystalline silicoaluminophosphates. The pores have a nominal diameter of greater than about 3 Å. The "essentially empirical composition" is $mR:(Si_xAl_yP_z)O_2$, where R represents at least one organic templating agent present in the intracrystalline pore system; m has a typical value of from 0 to 0.3 and represents the moles of R present per mole of $(Si_xAl_yP_z)O_2$; x, y and z represent the mole fractions of silicon, aluminum and phosphorus, respectively, present as tetrahedral oxides. The fractions are such that they are within a pentagonal compositional area defined by points A, B, C, D and E of the ternary diagram of FIG. 1 and preferably within the pentagonal compositional area defined by points a, b, c, d and e of FIG. 2, of the drawings of the patent. The SAPO molecular sieves have a characteristic x-ray powder diffraction pattern which contains at least the d-spacings set forth in any one of Tables I, III, V, VII, IX, XI, XIII, XV, XVII, XIX, XXI, XXIII or XXV of the patent. Further, the as-synthesized crystalline silicoaluminophosphates of the patent may be calcined at a temperature sufficiently high to remove at least some of any organic templating agent present in the intracrystalline pore system as a result of such synthesis. The silicoaluminophosphates are generally referred to therein as "SAPO", as a class, or as "SAPO-n" wherein "n" is an integer denoting a particular SAPO as its preparation is reported in the patent.

The U.S. patent speaks at column 8, lines 12-16 of employing seed crystals to generate SAPO species. That technique is described in examples 22, 51 and 53.

U.S. Ser No. 600,312 filed Apr. 13, 1984, commonly assigned, EPC Public. 0 159 624, published Oct. 30, 1985

ELAPSO molecular sieves have the units $ELO_2^n$, $AlO_2^-$, $PO_2^+$, $SiO_2$ in the framework structure and have an empirical chemical composition on an anhydrous basis expressed by the formula:

$mR:(EL_wAl_xP_ySi_z)O_2$ where "EL" represents at least one element present as a framework oxide unit "$ELO_2^n$" with charge "n" where "n" may be $-3$, $-2$, $-1$, 0 or $+1$; "R" represents at least one organic templating agent present on the intracrystalline pore system; "m" represents the molar amount of "R" present per mole of $(EL_wAl_xP_ySi_z)O_2$ and has a value from zero to about 0.3; and "w", "x", "y" and "z" repesent the mole fractions of $ELO_2^n$, $AlO_2^-$, $PO_2^+$, $SiO_2$, respectively present as framework oxide units. "EL" is characterized as an element having (a) a mean "T-O" distance in tetrahedral oxide structures between about 1.51 Å and about 2.06 Å, (b) a cation electronegativity between about 125 kcal/g-atom to about 310 kcal/gm-atom and (c) a capability of forming stable M-O-P, M-O-Al or M-O-M bonds in crystalline three dimensional oxide structures having a "m-O" bond dissociation energy greater than about 59 kcal/g-atom at 298° K. "w", "x", "y" and "z" represent the mole fractions of "EL", aluminum, phosphorus and silicon, respectively, present as framework oxides. The mole fractions are within the limiting compositional values or points as follows:

| Point | Mole Fraction | | |
|---|---|---|---|
| | x | y | (z + w) |
| A | 0.60 | 0.39 − (0.01 p) | 0.01(p + 1) |
| B | 0.39 − (0.01 p) | 0.60 | 0.01(P + 1) |
| C | 0.01 | 0.60 | 0.39 |
| D | 0.01 | 0.01 | 0.98 |
| E | 0.60 | 0.01 | 0.39 | where "p" is an integer corresponding to the number of elements which "EL" represents in the $(EL_wAl_xP_ySi_z)O_2$ composition.

The "EL" of the "ELAPSO" molecular sieves may be defined as representing at least one element capable of forming a framework tetrahedral oxide and is preferably selected from the group consisting of arsenic, beryllium, boron, chromium, cobalt, gallium, germanium, iron, lithium, magnesium, manganese, titanium and zinc and "w", "x", "y" and "z" represent the mole fractions of "EL", aluminum, phosphorus and silicon, respectively, present at tetrahedral oxides in which the mole fractions are within the limiting compositional values or points as follows:

| Point | Mole Fraction | | |
|---|---|---|---|
| | x | y | (z + w) |
| a | 0.60 | 0.39 − (0.01 p) | 0.01(p + 1) |
| b | 0.39 − (0.01 p) | 0.60 | 0.01(p + 1) |
| c | 0.10 | 0.55 | 0.35 |
| d | 0.55 | 0.10 | 0.35 | where "p" is as above defined.

The EP publication at page 16 discloses the use of crystalline and amorphous aluminophosphate as a source of phosphorus and aluminum and at page 17 describes seeding the reaction mixture. Examples 11A, 12A, 93A-103A, 5B, 6B, 55B, 58B, 59B, 50D-56D, 59D-62D and 12F-15F depict the use of seed crystals.

U.S. Pat. No. 4,500,651, patented Feb. 19, 1985

TAPO molecular sieves comprise three-dimensional microporous crystalline framework structures of [TiO₂], [AlO₂] and [PO₂] tetrahedral units which have a unit empirical formula on an anhydrous basis of:

$$mR:(Ti_xAl_yP_z)O_2 \quad (1)$$

wherein "R" represents at least one organic templating agent present in the intracrystalline pore system; "m" represents the moles of "R" present per mole of $(Ti_xAl_yP_z)O_2$ and has a value of from zero to 5.0, the maximum value in each case depending upon the molecular dimensions of the templating agent and the available void volume of the pore system of the particular titanium molecular sieve; "x", "y" and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | (z + w) |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.0001 | 0.70 | 0.299 |

The parameters "x", "y" and "z" are preferably within the following values for "x", "y" and "z":

| Point | Mole Fraction | | |
|---|---|---|---|
| | x | y | (z + w) |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The TAPO molecular sieves are generally further characterized by an intracrystalline adsorption capacity for water at 4.6 torr and about 24° C., of about 3.0 weight percent. The adsorption of water has been observed to be completely reversible while retaining the same essential framework topology in both the hydrated and dehydrated state.

The U.S. patent at column 8, lines 65–68, and column 9, lines 15–18, discusses the use of crystalline amorphous aluminophosphate as a source of phosphorus and aluminum. At column 6, lines 1–5, seeding is described as facilitating the crystallization procedure. Comparative example 44 describes a composition of amorphous TiO₂ and 95 wt. % AlPO₄18 without an indication of how the composition was prepared.

U.S. Pat. No. 4,684,617; EPC Publication 0 161 488, published Nov. 21, 1985

The TiAPSO molecular sieves have three-dimensional microporous framework structures of TiO₂, AlO₂⁻, PO₂⁺ and SiO₂ tetrahedral oxide units having an empirical chemical composition on an anhydrous basis expressed by the formula:

$$mR:(Ti_wAl_xP_ySi_z)O_2$$

wherein "R" represents at least one organic templating agent present in the intracrystalline pore system; "m" represents the molar amount of "R" present per mole of $(Ti_wAl_xP_ySi_z)O_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined in respect to the ternary diagram of FIG. 1 of the applications as being within the following limiting compositional values or points:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d of the ternary diagram of FIG. 2 of the aplications, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication, at page 13, describes the use of crystalline or amorphous aluminophosphate as a source of phosphorus and aluminum and, at page 14, points out that seeding the reaction mixture facilitates the crystallization procedure.

U.S. Pat. No. 4,554,143, patented Nov. 19, 1985

Ferroaluminophosphates (FAPO's) are disclosed in U.S. Pat. No. 4,554,143, incorporated herein by reference, and have a three-dimensional microporous crystal framework structure of AlO₂, FeO₂ and PO₂ tetrahedral units and have an essential empirical chemical composition, on an anhydrous basis, of:

$$mR:(Fe_xAl_yP_z)O_2$$

wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y" and "z" represent the mole fractions of iron, aluminum and phosphorus, respectively, present as tetrahedral oxides, representing the following values for "x", "y" and "z":

| Point | Mole Fraction | | |
|---|---|---|---|
| | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferrosluminophosphates the values of "x", "y" and "z" in the formula above are representing the following values of "x", "y" and "z":

| Point | Mole Fraction | | |
|---|---|---|---|
| | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the $FeO_2$ structural units can be in either the ferric or ferrous valence state, depending largely upon the source of the iron in the synthesis gel. Thus, a $FeO_2$ tetrahedron in the structure can have a net charge of either $-1$ or $-2$.

The patent indicates at column 5, lines 43–45 and 54–56, that crystalline amorphous aluminophosphate may be used as a source of phosphorus and aluminum and at column 6, lines 1–5, describes seeding of the reaction mixture as facilitating the crystallization procedure.

U.S. Pat. No. 4,683,217; EPC Publication 0 161 491, published Nov. 21, 1985

The FeAPSO molecular sieves have a three-dimensional microporous crystal framework structures of $FeO_2^{-2}$ (and/or $FeO_2$), $AlO_2$, $PO_2$ and $SiO_2$ tetrahedral oxide units and having a unit empirical formula, on an anhydrous basis, of:

$$mR:(Fe_wAl_xP_ySi_z)O_2 \quad (1)$$

wherein "R" represents at least one organic templating agent present in the intracrystalline pore system; "m" represents the moles of "R" present per mole of $(Fe_wAl_xP_ySi_z)O_2$ and has a value of from zero to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication, at page 12, describes the use of seeding the reaction mixture to facilitate the crystallization procedure. At page 18, the publication describes the use of crystalline amorphous aluminophosphates as a source of phosphorus and aluminum in making the molecular sieve.

U.S. Ser. No. 600,170, EPC Publication 0 158 975, published Oct. 23, 1985

The ZnAPSO molecular sieves of U.S. Ser. No. 600,170, filed Apr. 13, 1984 comprise framework structures of $ZnO_2^{-2}$, $AlO_2^-$, $PO_2^+$ and $SiO_2$ tetrahedral units havings an empirical chemical composition on an anhydrous basis expressed by the formula:

$$mR:(Zn_wAl_xP_ySi_z)O_2$$

wherein "R" represents at least one organic templating agent present in the intracrystalline pore system; "m" represents the molar amount of "R" present per mole of $(Zn_wAl_xP_ySi_z)O_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication at page 13 discloses that crystalline or amorphous aluminophosphate may be used as a source of phosphorus or aluminum and at page 14 indicates that seeding of the reaction mixture with said crystals facilitates the crystallization procedure. Examples 12–15 are stated to employ the seeding procedure.

U.S. Pat. No. 4,758,419; EPC Publication 0 158 348, published Oct. 16, 1985

The MgAPSO molecular sieves have three-dimensional microporous framework structures of $MgO_2^{-2}$, $AlO_2^-$, $PO_2^+$ and $SiO_2$ tetrahedral oxide units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value from zero to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication depicts seeding to generate product at page 14 and in examples 5, 6, 55, 58 and 59.

U.S. Pat. No. 4,686,092; EPC Publication 0 161 480, published Nov. 11, 1985

The MnAPSO molecular sieves of U.S. Ser. No. 600,175, filed Apr. 13, 1984 having a framework structure of $MnO_2^2$, $AlO_2$, $PO_2$, and $SiO_2$ tetrahedral units having an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w., x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication at page 13 describes the use of crystal or amorphous aluminophosphate as a source of phosphorus or aluminum, and at page 14 characterizes the use of said crystals to facilitate the crystallization procedure. Examples 54–56 and 59–62 state said crystals were used in the manufacture of the MnAPSO products.

U.S. Pat. No. 4,744,970; EPC Publication 0 161 489, published Nov. 21, 1985

The CoAPSO molecular sieves of U.S. Ser. No. 600,174, filed Apr. 13, 1984 have three-dimensional microporous framework structures of $CoO_2^2$, $AlO_2$, $PO_2$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represents the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of the CoAPSO molecular sieves the values "w", "x", "y" and "z" in the above formula are within the limiting compositional values or points as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |

-continued

| | Mole Fraction | | |
|---|---|---|---|
| Point | x | y | (z + w) |
| d | 0.55 | 0.10 | 0.35 |

The EP publication at page 13 depicts the use of crystalline amorphous aluminophosphate as a source of phosphorus and aluminum and at page 14 states that seeding the reaction mixture facilitates the crystallization procedure. Examples 11, 12, 13, 93 and 97–103 depict the use of seed crystals.

U.S. Ser. Nos. 599,771 599,776 599,807, 599,809, 599,811 599,812 599,813 600,166 each filed Apr. 13, 1984, all now abandoned; U.S. Pat. No. 4,686,093; EPC Publication 0 158 976, published Oct. 23, 1985

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,028. Members of this novel class of compositions have a three-dimensional microporous crystal framework structure of $MO_2^2$, $AlO_2$ and $PO_2$ tetrahedral units and have the essentially empirical chemical composition, on an anhydrous basis, of:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y" and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y" and "z":

| | Mole Fraction | | |
|---|---|---|---|
| Point | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| | Mole Fraction | | |
|---|---|---|---|
| Point | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as-synthesized compositions are capable of withstanding 350° C. calcination in air for extended periods, i.e., at least 2 hours, without becoming amorphous.

The EP publication at pages 14 and 15 depicts the use of crystalline and amorphous aluminophosphate as a source of phosphorus and aluminum and at page 15 states that seeding the reaction mixture facilitates the cyrstallization procedure. Example 8 dicloses seeding of crystals.

EPC Applic. 85104386.9, filed Apr. 11, 1985 (EPC Publication No. 0158976, published Oct. 13, 1985) and EPC Applic. 85104388.5, filed Apr. 11, 1985 (EPC Publication No. 158348, published Oct. 16, 1985)

"ELAPO" molecular sieves are a class of crystalline molecular sieves in which at least one element capable of forming a three-dimensional microporous framework form crystal framework structures of $AlO_2$, $PO_2$ and $MO_2$ tetrahedral oxide units wherein "$MO_2$" represents at least one different element (other than Al or P) present as tetrahedral oxide units "$MO_2$" with charge "n" where "n" may be −3, −2, −1, 0 or +1. The members of this novel class of molecular sieve compositions have cyrstal framework structures of $AlO_2$, $PO_2$ amd $MO_2$ tetrahedral units and have an empirical chemical composition on an anhydrous basis expressed by the formula:

$$mR:(M_xAl_yP_z)O_2$$

wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different elements ($M_1$) such that the molecular sieves contain at least one framework tetrahedral units in addition to $AlO_2$ and $PO_2$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc.

The ELAPO molecular sieves are generally referred to herein by the acronym or "ELAPO" to designate element(s) "M" in a framework of $AlO_2$, $PO_2$ and $MO_2$ tetrahedral oxide units. Actual class members will be identified by replacing the "EL" of the acronym with the elements present as $MO_2$ tetrahedral units.

When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2$, $PO_2$ and $MO_2$ tetrahedral units and have an empirical chemical composition on an anhydrous basis expressed by the formula:

$$mR:(M_xAl_yP_z)O_2;$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M" aluminum and phosphorus are expressed by the empirical chemical formula (anhydrous):

$$mR:(M_xAl_yP_z)O_2$$

where "x", "y" and "z represent the mole fractions of said "M", aluminum and phosphorus. The individual mole fractions of each "M" (of when M denotes two or more elements, $M_1$, $M_2$, $M_3$, etc.) may be represented by "$x_1$", "$x_2$", "$x_3$", etc. wherein "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x" hereinafter, where "$x_1$"+"$x_2$"+"$x_3$" ... ="x" and where $x_1$, $x_2$, $x_3$, etc. are each at least 0.01.

The ELAPO molecular sieves have crystalline three-dimensional microporous framework structures of $MO_2$, $AlO_2$ and $PO_2$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|---|---|---|---|
| | x | y | (z + w) |
| A | 0.02 | 0.60 | 0.38 |
| B | 0.02 | 0.38 | 0.60 |
| C | 0.39 | 0.01 | 0.60 |
| D | 0.98 | 0.01 | 0.01 |
| E | 0.39 | 0.60 | 0.01 |

In a preferred sub-class of the ELAPOs of this invention, the values of "x", "y" and "z" in the formula above are within the following values of "x", "y" and "z":

| Point | Mole Fraction | | |
|---|---|---|---|
| | x | y | (z + w) |
| a | 0.02 | 0.60 | 0.39 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |

| Point | Mole Fraction | | |
|---|---|---|---|
| | x | y | (z + w) |
| f | 0.39 | 0.60 | 0.01 |

U.S. Pat. No. 4,310,440

ALPO's are the basic and simplest of the crystalline aluminophosphates. They each having a framework structure whose chemical composition expressed in terms of mole ratios of oxides is:

$$Al_2O_3:1.0\pm0.2P_2O_5:$$

each of said framwork structures being microporous in which the pores are uniform and have nominal diameters within the range of about 3 to about 10 Å, an intracrystalline adsorption capacity for water at 4.6 torr and 24° C. of at least 3.5 weight percent, the adsorption and desorption of water being completely reversible while retaining the same essential framework topology in both the hydrated and dehydrated state.

U.S. Pat. Applications 600,168, (abandoned) 600,182, (abandoned) 600,183; U.S. Pat. No. 4,741,892; European Patent Publ. 0 158 350, publ. Oct. 16, 1985

SENAPSO are quinary and senary molecular sieves that have framework structures of at least two elements having tetrahedral oxide units "$MO_2^n$" and having $AlO_2^-$, $PO_2^+SiO_2$ tetrahedral oxide units, where "n" is $-3$, $-2$, $-1$, 0 or $+1$, and have an empirical chemical composition on an anhydrous basis expressed by the formula:

$$mR:(M_wAl_xP_ySi_z)O_2$$

wherein "R" represents at least one organic templating agent present in the intracrystalline pore system; "m" represents the molar amount of "R" present per mole of $(M_wAl_xP_ySi_z)O_2$ and has a value of from 0 to about 0.3; "M" represents at least two elements selected from the group consisting of arsenic, beryllium, boron, chromium, cobalt, gallium, germanium, iron, lithium, magnesium, manganese, titanium, vanadium, and zinc; "n" is as above defined; and "w", "x", "y" and "z" represent the mole fractions of elements "M", aluminium, phosphorus and silicon, respectively, present as tetrahedral oxides, each having a value of at least 0,01.

The publication, at pages 14–15, generally described seeding reaction mixtures to form the desired product.

Zeolitic molecular sieves may be represented by the general formula:

$$Me_{x/n}[(AlO_2)_x(SiO_2)y]\cdot zH_2O$$

where Me is a metal cation, x/n is the number of exchangeable metal cations of valence n, x is also the number of aluminum ions combined in the form of aluminate, y is the number of silicon atoms and z is the number of water molecules, removal of which produces the characteristic pore or channel system. The ratio z/x is a number from 1 to 5, usually from 1 to 2.

Typical of the zeolitic molecular sieves are chabazite, faujasite levynite, Linde Type A, gismondine, erionite, sodalite, Linde Type X and Y, analcime, gmelinite, harmotome, levynite, mordenite, epistilbite, heulandite, stilbite, edingtonite, mesolite, natrolite, scolecite, thomsonite, brewsterite, laumontite, phillipsite, the ZSM's (e.g., ZSM-5[2], ZSM-20[3], ZSM-12[4], ZSM-34[5], etc.) and Beta[6] and the like. Typical of suitable zeolitic molecular sieves employable in the practice of this invention are the following:

Zeolites-A, AgX, AgY, AlHY, alkylammonium X and Y, BaX, BaY, BeY, Ca-A, Ca-near faujasite, Ca-HX, Ca-X, Ca-Y, CdX, CdY, CeY, CoA, CoX, CoY, CrY, CsL, CsX, CsY, Cu-X, Cu-Y, Cu-diethylammonium Y, Cu-ethylammonium Y, Fe-X, Fe-Y, group IAX, group IAY, group IIAY, HY, KL, KX, KY, L, La-X, La-Y, LiA, LiY, LZ-10, LZ-210, MgHY, MgNa, MgNH$_4$Y, MgX, MgY, MnX, MnY, Na-A, Na-near faujasite, Na-L, Na-X, Na-Y, NH$_4$L, NH$_4$X, NH$_4$Y, Ni-A, Ni-X, Ni-Y, omega, PdY, phosphate, Pt, rare earth X, rare earth Y, RbX, RhY, SrX, SrY, steam stabilized or ultra-stable Y, tetramethylammonium Y, TIX, triethylammonium Y, X, Y, Y-82, ZK-5, Zn-mordenite, Zn-X, An-Y, the ZSM's supra, and the like.

[2]See U.S. Pat. No. 3,702,886.
[3]See U.S. Pa. No. 3,972,983.
[4]See U.S. Pat. No. 3,832,449.
[5]See U.S. Pat. No. 4,079,095.
[6]See U.S. Pat. No. 3,308,069 and U.S. Re. Pat. No. 28,341.

Other zeolitic CMSCs useful in the present invention include boron-treated aluminosilicates, such as described in U.S. Pat. No. 4,613,720. Other NZMSs include the silica molecular sieves, such as silicalite as depicted in U.S. Pat. No. 4,061,724.

The average diameter of the pores of the presently useful CMSCs is preferably in the range of about 3 angstroms to about 15 angstroms as determined by measurements described in "Zeolite Molecular Sieves" by Donald W. Breck, published by John Wiley & Sons, New York, 1974. This average diameter is referred to as the average effectie diameter. When the feedstock and desired product or products are relatively small, e.g., organic components containing 1 to about 10 and preferably 1 to about 4 carbon atoms per molecule, the CMSC preferably has pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the CMSC and adsorption of the adsorbate is over three percent by weight of the adsorbate based on the weight of the CMSC. Certain of the CMSCs useful in the present invention have pores with an average effective diameter in the range of about 3 angstroms to about 5 angstroms.

The presently useful catalysts may be incorporated into solid particles in which the catalyst is present in an amount effective to promote the desired chemical conversion. In one embodiment, the solid particles comprise a catalytically effective amount of the catalyst and at least one of a filler material and a binder material to provide a desired property or properties, e.g., desired catalyst dilution, mechanical strength and the like, to the solid particles. Such filler and binder materials, i.e., matrix materials, are to some extent porous in nature and may or may not be effective to promote the desired chemical conversion. Such matrix materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-alumina-zirconias, mixtures of these and the like.

If one or more matrix materials are included in the solid particles, the catalyst preferably is included in solid particles containing no more than about 75%, more preferably no more than about 35%, by weight of other solid material, e.g., matrix materials. The amount of matrix materials included in the present solid particles is preferably reduced relative to the amount of such materials employed in solid particles of a fixed bed catalyst or solid particles of a fluidized bed catalyst used to promote the same chemical conversion. It has been found that the solid particles in the slurry reaction system of the present invention are not subjected to the relatively frequent and often wide temperature and other condition changes to which a fixed bed catalyst is subjected, or to the turbulent, attrition causing movement to which a fluid bed catalyst is subjected. Thus, the present slurry catalysts require less of the protection normally afforded to fixed bed and fluid bed catalysts by such matrix materials. The reduced amount of matrix materials may also provide improved overall process performance since such materials often promote undesired chemical reactions. Therefore, reduced amounts of such materials may result in less undesired products. In one embodiment, substantially pure catalyst, i.e., catalyst particles substantially free of matrix materials, are used in the present slurry reaction system.

The preparation of solid particles comprising CMSC and matrix materials is conventional and well known in the art and, therefore, need not be discussed in detail here. Certain of such preparation procedures are described in the patents and patent applications previously incorporated by reference herein, as well as in U.S. Pat. Nos. 3,140,253 and RE. 27,639. Catalysts which are formed during and/or as part of the methods of manufacturing the solid particles are within the scope of the present invention.

The solid particles including the catalysts may be of any size functionally suitable in the present invention. In order that the catalyst can be utilized more effectively, the solid particles are preferably small relative to fixed bed solid particles used to promote similar chemical conversions. More preferably, the solid particles have a maximum transverse dimension, e.g., diameter, in the range of about 1 micron to about 500 microns, still more preferably about 25 microns to about 200 microns.

The catalyst and/or solid particles may be subjected to mechanical size reduction, e.g., grinding, crushing, milling and the like, in order to obtain the desired particle size. However, it is preferred that the solid particles including the catalyst be more smooth, and more preferably also more spherical, relative to solid particles, of similar composition obtained by mechanical size reduction. Such particle smoothness and sphericity tends to improve the flow properties and useful life of the slurry and may also allow increased solids loading in the slurry, if desired. One particularly useful processing step to achieve such smoothness and sphericity is to employ spray drying as part of the solid particle manufacturing process to form the solid particles of precursors of the solid particles. An additional advantage of employing such spray drying is that the conditions of such a step can be controlled so that the product solid particles are of a desired particle size or size range. The use of spray drying in such catalyst/solid particle manufacturing is conventional and well known, and therefore need not be discussed in detail here.

The non-zeolitic molecular sieves or NZMSs are particularly useful in the practice of the present invention. Among the NZMSs, the SAPOs are particularly useful. SAPO-17 and SAPO-34, which is described in detail in Example 38, of U.S. Pat. No. 4,440,871, are especially preferred catalysts for promoting the reaction of molecules containing one carbon atom, e.g., methane, methanol, methyl halide, and the like, to form products containing up to about 6, preferably up to about 4, carbon atoms per molecule, e.g., ethylene, propylene, butylene and the like. currently, SAPO-34 is most preferred.

The amount of catalyst or solid particles in the slurry, i.e., made up of such solids and the suspending, substantially non-reactive liquid, may vary over a wide range depending, for example, on the specific processing application involved. Relatively high loadings of catalyst-/solid particles in the slurry may be appropriate in order to contact the feedstock and catalyst in a space and time effective manner. On the other hand, excessive catalyst-/solid particle loadings are to be avoided since reduced desired product might result. Also, the slurry may have to be flowable or pumpable to move the slurry to another vessel, if desired, for catalyst regeneration. Preferably, the catalyst/solid particles comprise about 0.1% to about 50%, more preferably about 0.2% to about 30%, by weight of the slurry.

One important feature of the present invention is the use of a suspending liquid in the presently useful slurry which is less reactive than the feedstock. That is, the suspending liquid is less likely to chemically react, e.g., by itself or with the feedstock, product and diluent (if any), at the conditions of the feedstock/catalyst contacting step. Thus, the rate of chemical conversion or reaction of the suspending liquid is reduced, preferably substantially reduced, relative to such rate for the feedstock at the conditions of the feedstock/catalyst contacting step. More preferably, the suspending liquid is substantially non-reactive, i.e., does not substantially chemically react or is substantially chemically inert, at the conditions of the present feedstock/catalyst contacting step, particularly with regard to chemical reactions promoted by the presently useful catalyst. The suspending liquid may degrade or deteriorate, e.g., by oxidation, thermal cracking and the like, over a relatively long period of time at contacting conditions, e.g., elevated temperature. Such degradation or deterioration may result in replacing the suspending liquid, but should not be considered in determining whether the liquid is substantially non-reactive. Preferably, the composition of the suspending liquid is chosen so that the size and/or shape of the liquid's molecules are inconsistent with access to the pores of the catalyst. For example, the molecules of the liquid may be too big to enter the pores of the catalyst.

The suspending liquid may be chosen from a wide variety of compositions provided it functions as described herein. The liquid should be stable, i.e., substantially resistant to deterioration or decomposition at catalyst/feedstock contacting conditions, which often include elevated temperatures, for example, in excess of about 300° C. In one embodiment, the molecules of the suspending liquid have a kinetic diameter or diameters of a size to substantially prevent such molecules from entering the pores of the catalyst. The liquid may be inorganic or organic. One or more silicones and the like materials may be used as the suspendng liquid. Suitable organic liquids preferably include carbon and hydrogen, and more preferably further include at least one other element, for example, halogen, nitrogen, oxygen, phosphorus, sulfur and mixtures thereof, with liquids comprising carbon, hydrogen and oxygen-containing molecules being particularly useful. Suspending liquids selected from the group consisting of dibenzyl benzenes, diphenyl ether and mixtures thereof have been found to be especially useful, particularly when the molecules of the feedstock contain one carbon atom.

The suspending liquid is preferably chosen so that the feedstock is more soluble than the desired conversion product (or products) in the liquid at the feedstock-/catalyst contacting conditions. The solubility of the feedstock in the suspending liquid facilitates effective feedstock/catalyst contacting, while the relative insolubility of the desired product in the liquid facilitates separation of the desired products from the catalyst and reduces the destruction, e.g., further chemical conversion, of the desired product to help preserve the desired product. More preferably, the desired product or products are substantially insoluble in the suspending liquid at the feedstock/catalyst contacting conditions.

In one embodiment, the suspending liquid includes at least one component effective to improve at least one property of the catalyst. In the context of this paragraph, the term "catalyst" refers not only to the CMSC itself, but also to the other components, if any, of the solid particles, e.g., matrix materials, as well. Thus, for example, if the binder material is benefited by a component in the liquid and, as a result, the overall performance of the catalyst is improved, at least one property of the catalyst is improved. Therefore, such beneficiation of other component or components of the solid particles is within the scope of this embodiment of the present invention. The selectivity of the catalyst to the desired products is one particularly useful property that can be improved by a component of the suspending liquid. In situations where the CMSC is present in solid particles containing one or more matrix materials, the suspending liquid preferably includes at least one component to reduce the undesired catalytic activity of such matrix material or materials. In one particular embodiment, the component in the liquid is a base the molecules of which are substantially prevented, e.g., because of size and/or shape and/or transition stage considerations, from entering the pores of the CMSC. Such base acts to inactivate or reduce the undesired catalytic activity of the matrix materials without substantially affecting the desired catalytic activity of the catalyst. The base is preferably selected from the group consisting of pyridine, pyridine derivatives, quinoline, quinoline derivatives and mixtures thereof, particularly when the preferred relatively small effective pore diameter CMSCs are employed. The amount of such components or components included in the suspending liquid may vary over a wide range, provided that such component is effective to improve at least one property of the catalyst. Such component is preferably present in an amount in the range of about 0.001% to about 20%, more preferably about 0.1% to about 15%, by weight of the liquid in the slurry. Such component may be periodically or continuously added to the suspending liquid to provide the desired effect on a continuing basis.

Materials in the supercritical state act substantially like liquids. Therefore, in certain embodiments, materials such as carbon dioxide, water and the like, in the supercritical state may be employed as the present suspending liquids. Thus, supercritical materials which are capable of functioning as suspending liquids in the present invention and otherwise meet the criteria for suspending liquids set forth herein are included within the scope of the present invention as suspending liquids.

The chemical conversion or reaction obtained by practicing the present invention can vary widely and depends, for example, on the feedstock and catalyst employed and on the feedstock/catalyst contacting conditions used. Substantially any chemical conversion or reaction which is capable of being catalyzed by a CMSC and conducted in a slurry system may be conducted while practicing the present invention. Examples of reactions which may be obtained include cracking; disproportionation; olefin production from non-olefin feedstocks; olefin interconversion; aldol, e.g., aldehyde-aldehyde, ketone-ketone, aldehyde-ketone and aldehyde or ketone-aromatic component, condensation; condensation reactions to produce cyclic lactams; isoprene formation; alkylation (aromatic, e.g., benzene, toluene and phenol alkylation); and isomerization (xylene isomerization). One particularly preferred chemical conversion or reaction involves olefin production from non-olefin feedstocks, more preferably feedstocks comprising aliphatic hetero compounds.

Substantially any feedstock or combination of feedstocks may be employed in the present invention. Such feestock, i.e., reactant component or components, may be gaseous, solid or liquid at ambient conditions, i.e., 20° C. and at atmospheric pressure. The feedstock may be inorganic, organic or a combination of inorganic and organic components. The present reaction system is particularly applicable to organic feedstocks, preferably having molecules comprising carbon and hydrogen, and more preferably at least one other element. This other element is preferably selected from the group consisting of oxygen, sulfur, halogen, nitrogen, phosphorus and mixtures thereof, with oxygen being particularly preferred.

As alluded to previously, the present invention is particularly useful in converting feedstocks having relatively small molecules, i.e., molecules having relatively small kinetic diameters. Thus, the feedstock preferably contains 1 to about 10, more preferably 1 to about 4, carbon atoms per molecule. Aliphatic hetero compounds are particularly preferred feedstocks for use in the present invention, especially when light olefins, i.e., olefins containing 2 to about 6 and preferably 2 to 4 carbon atoms per molecule, are to be produced. When light olefins are the desired product, such olefins are preferably produced as the major hydrocarbon product, i.e. over 50 mole percent of the hydrocarbon product is light olefins. The term "aliphatic hetero compounds" is employed herein to include alcohols, halides, mercaptans, sulfides, amines, ethers and carbonyl compounds (aldehydes, ketones, carboxylic acids and the like). The aliphatic moiety preferably contains from 1 to about 10 carbon atoms and more preferably contains from 1 to about 4 carbon atoms. Suitable reactants include lower straight or branched chain alkanols, their unsaturated counterparts, and the nitrogen, halogen and sulfur analogue of such. Representative of suitable aliphatic hetero compounds include: methanol; methyl mercaptan; methyl sulfide; methyl amine; dimethyl ether; ethanol; ethyl mercaptan; ethyl chloride; diethyl ether; methyethyl ether; formaldehyde; dimethyl ketone; acetic acid; n-alkyl amines; n-alkyl halides and n-alkyl sulfides having n-alkyl group having 3 to 10 carbon atoms; and mixtures thereof. In one embodiment, e.g., where light olefins are the desired products, the feedstock is preferably selected from the group consisting of methanol, ethanol, dimethyl ether, diethyl ether and mixtures thereof, with methanol being particularly preferred.

In certain instances, it is preferred that the feedstock/catalyst contacting conditions be such that the contacting temperature exceed the critical temperature of the feedstock. In other words, in certain embodiments, the feedstock is preferably in the supercritical state at the feedstock/catalyst contacting conditions. Having the feedstock in the supercritical state is particularly useful when the feedstock contains 1 to about 10, more preferably 1 to about 4, carbon atoms per molecule.

The product or products obtained from the feedstock/catalyst contacting will, of course, depend, for example, on the feedstock, catalyst and conditions employed. As with the feedstock, the product or products can be inorganic, organic or a combination of inorganic and organic components. Preferably, the desired product is organic. However, it should be noted that a necessary, and therefore desired, reaction by-product may be inorganic even when the primary product sought is organic. This is exemplified by the conversion of methanol to light olefins plus water. The organic product or products have molecules which preferably include carbon and hydrogen. In one embodiment, the desired product preferably contains 1 to about 10, more preferably 1 to about 4, carbon atoms per molecule. The desired product or products preferably have kinetic diameters which allow such product or products to be removed from or escape from the pores of the sieving catalyst. After leaving the catalyst pores, the product or products preferably are in a form, more preferably in a gaseous form, easily separable from the slurry.

In addition to the feedstock, a diluent may be used in conjunction with the feedstock if desired and/or beneficial to the overall process. Such diluent may be mixed or combined with the feedstock prior to the feedstock/catalyst contacting or it may be introduced into the contacting zone separately from the feedstock. Preferably, the feedstock and diluent are both substantially continuously fed to the feedstock/catalyst contacting. Such diluent preferably acts to moderate the rate, and possibly also the extent, of the feedstock chemical conversion and may also act to aid in temperature control. In certain embodiments of the present invention, the amount of diluent used may be reduced relative to fixed catalyst bed and fluidized catalyst bed operations involving similar chemical conversions. Apparently, the suspending liquid performs one or more of the functions of the diluent. Thus, less diluent is required and savings in both capital investment and operating costs for commercial practice can be achieved.

Such diluent, although preferably chemically substantially non-reactive at the feedstock/catalyst contacting conditions, is clearly distinguished from the suspending liquid of the slurry. For example, the diluent is introduced in combination or conjunction with the feedstock and, therefore, may be considered a feedstock component, which the suspending liquid is most often not. The suspending liquid is liquid whereas the diluent most often is in the same phase with the feedstock. Also, the diluent includes molecules which preferably are sized to have access to the pores of the sieving catalyst whereas the suspending liquid preferably does not.

Typical of the diluents which may be employed in the instant prcess are helium, argon, nitrogen, carbon monoxide, carbon dioxide, hydrogen, water, hydrocarbons and mixtures thereof. When the feedstock contains 1 to about 10 carbon atoms per molecule, the diluent, if any, is preferably selected from the group consisting of helium, argon, nitrogen, carbon monoxide, carbon dioxide, hydrogen, water and mixtures thereof, with water, nitrogen and mixtures thereof, in particular water, being more preferred. The amount of diluent employed, if any, may vary over a wide range depending on the particular application involved. For example, the amount of diluent may be in an amount in the range of about 0.1% or less ot about 99% or more of the moles of feedstock.

The catalyst is preferably at least periodically contacted with regenerating medium to substantially maintain or improve the effectiveness of the catalyst to promote the desired chemical conversion. For example, the catalyst may become less effective due to carbonaceous deposits or precursors of such deposits in the pores or other parts of the catalyst. In one embodiment, the regeneration medium acts to reduce the average kinetic diameter of molecules present in the pores of the catalyst. Such reduction in the kinetic diameter of these molecules is preferably sufficient to allow the resulting molecules to leave or exit the catalyst pores, thereby providing more pores and/or pore volume for the desired chemical conversion. If regeneration is required, the sieving catalyst can be removed, preferably substantially continuously removed, from the feedstock/catalyst contacting zone, separated from the suspending liquid, and introduced, preferably substantially continuously introduced, into a regeneration zone where the catalyst can be regenerated, such as for example, by removing carbonaceous deposit material by oxidation in an oxygen-containing atmosphere. After such oxidative regeneration, the catalyst is preferably combined with the suspending liquid prior to being reintroduced, preferably substantially continuously reintroduced into the feedstock/catalyst contacting zone. If the suspending liquid is sufficiently stable during catalyst regeneration, the regeneration medium/catalyst contacting can be conducted while the catalyst is slurried with the suspending liquid.

In one embodiment, the catalyst includes at least one added component effective to promote the action of the regeneration medium, For example, the catalyst may include at least one metal component effective to promote the oxidation of the carbonaceous deposit material. Of course, such metal component should have no substantial adverse effect on the desired chemical conversion. The specific added catalyst component depends on the requirement of the particular application involved. Examples of such added components include components of transition metals, such as nickel, cobalt, iron, manganese, copper and the like; the platinum group metals such as platinum, palladium, rhodium and the like; and the rare earth metals such as cerium, lanthanum and the like, and mixtures thereof. If an added metal component is used, it is preferred that this component be present at a minor amount, more preferably as about 1 ppm to about 20%, by weight (calculated as elemental metal) of the weight of catalyst, including the matrix materials, employed.

Alternately to the oxidative catalyst regeneration, a reducing medium can be employed to regenerate the catalyst. Such reducing medium, preferably selected from the group consisting of hydrogen, carbon monoxide and mixtures thereof, and in particular hydrogen, can, for example, be used to react with molecules, e.g., of carbonaceous deposit material precursor, in the pores of the catalyst to produce molecules of reduced kinetic diameter so that such produced molecules can exit the pores of the catalyst. In one embodiment, the reducing medium is hydrogen and the catalyst includes at least one component, preferably a metal component, effective to promote hydrogenation and/or hydrocracking of molecules present in the pores of the catalyst at the conditions of the reductive regeneration.

The use of a reducing medium in catalyst regeneration may provide advantages. For example, if the suspending liquid is sufficiently stable to be substantially inert to the reducing medium, the catalyst can be regenerated in the slurry, preferably in the feedstock/catalyst contacting zone or zones. Combinations of oxidative and reductive catalyst regeneration may be employed. For example, the use of a reducing medium, e.g., as a diluent as discussed herein, may at least partially regenerate the catalyst, thereby prolonging the useful cycle life before the catalyst is subjected to a more complete oxidative regeneration. Of course, both the oxidative regeneration and reductive regeneration of the catalyst may be used, as appropriate, alone rather than in combination.

The instant process may be carried out in a batch, semi-continuous, or continuous fashion, with continuous operation being preferred. The process can be conducted in a single feedstock/catalyst contacting zone or a plurality of such zones arranged in series or in parallel. After the desired product or products are separated from the slurry, various techniques, such as distillation, adsorption and the like, can be used to recover or purify such product or products.

The conditions of feestock/catalyst contacting can vary widely depending, for example, on the specific feedstock, suspending liquid and catalyst employed and on the specific product or products desired. Such conditions preferably are sufficient to maintain the suspending liquid substantially in the liquid phase. The present process is particularly applicable with feedstock/catalyst contacting temperatures in excess of about 200° C., more preferably in excess of about 300° C., and with feedstock/catalyst contacting pressures in excess of about 10 psig., more preferably in excess of about 50 psig. If light olefins are to be produced from feedstock containing 1 to about 4 carbon atoms per molecule, feedstock/catalyst contacting temperatures are preferably in the range of about 200° C. to about 600° C. or even about 700° C., more preferably about 250° C. to about 550° C. and still more preferably about 300° C. to about 500° C., with feedstock/catalyst contacting pressures preferably below about 1500 psig. The use of relatively elevated pressures may be advantageous in the present process relative to a fixed or fluidized catalyst bed process in which elevated pressure may result in operational difficulties and/or may adversely affect catalyst performance, e.g., selectively to the desired product or products. The residence times of the feedstock and the catalyst in the feedstock/catalyst contacting zone may be independently selected depending, for example on the specific feedstock, suspending liquid and catalyst employed and on the specific product or products desired.

The following non-limiting examples are provided to better illustrate the invention.

EXAMPLE 1

Twenty-five grams of a powdered Chabazite having an average particle diameter of 150 microns was used as catalyst. Chabazite is a small pore molecular sieve and is sold under the trademark AW 500 by Union Carbide Corporation. Chabazite is described in detail in "Zeolite Molecular Sieves" by Donald W. Breck, published by John Wiley & Sons, New York (1974), especially at page 38. This Chabazite was mixed with two liters of a liquid comprising primarily diphenyl ether and sold under the trademark Dowtherm A by Dow Chemical Company. The mixture was charged into an autoclave having a capacity of about four liters. The internal surfaces of the autoclave were stainless steel. The interior of the autoclave was pressurized with nitrogen to about 500 psig., and the heater and agitator associated with the autoclave was started. When the autoclave reached a temperature of 375° C., the internal pressure was 980 psig.

Fifty milliliters of a mixture of 50% by volume methanol and 50% by volume water was pumped into the autoclave over a period of about 12 minutes. Five minutes later, the product was sampled into a stainless steel sample bomb. An analysis of the sample is given in Table 1.

TABLE 1

| Component | Carbon Selectivity[1] |
|---|---|
| $CH_4$ | 11.79 |
| $C_2H_4$ | 36.85 |
| $C_2H_6$ | 3.15 |
| $C_3H_6$ | 16.40 |
| $C_3H_8$ | 24.30 |
| $C_4H_8$ | 6.02 |
| $C_5s$ | 0.35 |
| CO | 0.16 |
| $CO_2$ | 0.98 |

[1]Carbon Selectivity as used herein with respect to a given product is the percent of carbon atoms in the total listed products present in the given product.

Methanol conversion to the above products was about 63%, with about 37% of the feed methanol forming dimethyl ether.

EXAMPLE 2

Five grams of loose crystals of SAPO-34 was mixed with a mixture of 200 cc of water and two liters of Dowtherm A and charged into the autoclave as described in Example 1. The autoclave was purged extensively for thirty minutes with nitrogen to remove air and then heated to 375° C. At this point, the pressure was 500 psig. Fifty milliliters of a mixture of equal volumes of methanol and water was pumped into the autoclave over a period of 26 minutes while the slurry in the autoclave was agitated. Five minutes later, the product was sampled into a stainless steel sample bomb. An analysis of the sample is given in Table 2.

TABLE 2

| Component | Carbon Selectivity[1] |
|---|---|
| $CH_4$ | 6.93 |
| $C_2H_4$ | 30.33 |
| $C_2H_6$ | 2.51 |
| $C_3H_6$ | 28.91 |

TABLE 2-continued

| Component | Carbon Selectivity[1] |
|---|---|
| $C_3H_8$ | 9.14 |
| $C_4H_8$ | 18.28 |
| CO | 0.07 |
| $CO_2$ | 3.80 |

[1]Carbon Selectivity as used herein with respect to a given product is the percent of carbon atoms in the total listed products present in the given product.

Methanol conversion to the above products was 74.15%, with about 24.5% of the feed methanol forming dimethyl ether.

EXAMPLE 3

445 grams of ground Chabazite was mixed with two liters of Dowtherm A and charged to the autoclave described in Example 1. The autoclave was purged with nitrogen and pressurized to 200 psig. The autoclave was heated to 200° C. and repurged to remove any residual air. The pressure was built back to 100 psig. with nitrogen and the autoclave was heated to 375° C.

300 milliliters of methanol was pumped into the autoclave over a period of 19 minutes. Five minutes later, the product was sampled into a stainless steel sample bomb. An analysis of the sample is given in Table 3.

TABLE 3

| Component | Carbon Selectivity[1] |
|---|---|
| $CH_4$ | 27.94 |
| $C_2H_4$ | 34.19 |
| $C_2H_6$ | 1.44 |
| $C_3H_6$ | 8.11 |
| $C_3H_8$ | 14.18 |
| $C_4H_8$ | 4.27 |
| CO | 3.25 |
| $CO_2$ | 6.61 |

[1]Carbon Selectivity as used herein with respect to a given product is the percent of carbon atoms in the total listed products present in the given product.

Methanol conversion to the above products was 16.64%, with about 81% of the feed methanol forming dimethyl ether.

EXAMPLE 4

A material including a methanol to olefins catalyst used in certain of the following examples was prepared as follows:

A first slurry of 50% by weight SAPO-34 crystals and 50% by weight water was prepared and subjected to continuous mixing. In a separate vessel, a second, aqueous slurry of kaolin clay and aluminum hydroxychloride (which includes the equivalent of 23.4% by weight alumina, calculated as $Al_2O_3$) was prepared. The first slurry was added to the second slurry to form a combined slurry which was mixed for about 10 minutes. The combined slurry was then stone milled to obtain a substantially uniform particle distribution.

The milled slurry was then spray dried to produce particles having an average particle size of about 70 microns. The spray dried particles were calcined for two hours at 600° C.

The compositions of the first and second slurries were chosen so that the final particles contained 60% by weight SAPO-34, 23% by weight kaolin clay and 17% by weight $Al_2O_3$.

EXAMPLE 5

A slurry of 220 milliliters of Dowtherm A, 5 milliliters of quinoline, and 30 grams of the particles prepared in Example 4 was placed in a 300 milliliter autoclave.

740 milliliters of a feedstock containing 66 volume percent water and 34 volume percent methanol was supplied to the autoclave over a period of six hours. The reaction temperature was maintained at about 400° C. and the pressure was maintained at about 325 psig. After this period, the product was sampled into a stainless steel sample bomb. An analysis is given in Table 4.

TABLE 4

| Component | Carbon Selectivity[1] |
|---|---|
| $CH_4$ | 0.76 |
| $C_2H_4$ | 33.04 |
| $C_2H_6$ | 1.62 |
| $C_3H_6$ | 50.33 |
| $C_3H_8$ | 2.21 |
| $C_4H_8$ | 9.86 |
| $C_5$'s | 2.18 |
| CO | trace |
| $CO_2$ | trace |

[1]Carbon Selectivity as used herein with respect to a given product is the percent of carbon atoms in the total listed products present in the given product.

Methanol conversion to the above products was 92.8%.

EXAMPLES 6 TO 9

A slurry of 200 milliliters of a liquid mixture of isomeric dibenzyl benzenes, sold under the trademark Marlotherm S by Chemische Werke Huls Ag., 10 milliliters of quinoline, and 25 grams of the particles prepared in Example 4 was placed in a 300 milliliter autoclave.

The composition of the feed, which was fed continuously, was 87.08 volume percent water and 12.92 volume percent methanol. The temperature within the autoclave was maintained at about 390° C. to 410° C. and the pressure was maintained at 605 psig. The product from the autoclave was analyzed on a substantially continuous basis. Results of certain of these analyses, taken at various times, are shown in Table 5.

There was unreacted methanol in each of the products. None of these products included more than 0.10% by weight of dimethyl ether. The unreacted methanol can be separated out and recycled in a commercial embodiment.

After Examples 6 to 9, the slurry was removed from the autoclave and the catalyst was separated from the liquid by filtration. The catalyst is then placed in contact with air at 500° C. for 12 hours to regenerate the catalytic activity of the catalyst. After the treatment, the catalytic activity of the catalyst was substantially restored and it was used for another series of experiments, e.g., Examples 10 to 16 described below.

EXAMPLES 10 TO 16

A slurry of 200 milliliters of Marlotherm A, and 10 grams of the particles prepared in Example 4 and regenerated as noted above was placed in a 300 milliliter autoclave. This slurry included no quinoline.

The composition of the feed, which was fed continuously, was 87.08 volume percent water and 12.92 volume percent methanol. The temperature within the autoclave was maintained at about 355° C. to 375° C. and the pressure was maintained at about 615 psig to about 635 psig. The product from the autoclave was analyzed on a substantially continuous basis. Results of certain of these analyses, taken at various times, are shown in Table 6.

None of the products included more than 0.31% by weight of dimethyl ether.

TABLE 5

| EXAMPLE | TIME MINS. | METHANOL WHSV Hr.-1 | UNREACTED METHANOL C. S. % | CONVERSION % | $CH_4$ C. S. % | $C_2H_4$ C. S. % | $C_2H_6$ C. S. % | $C_3H_6$ C. S. % | $C_3H_8$ C. S. % | $C_4$s C. S. % |
|---|---|---|---|---|---|---|---|---|---|---|
| 6 | 45 | 2.77 | 20.59 | 79.4 | 0.97 | 10.56 | 1.03 | 41.57 | 17.02 | 21.64 |
| 7 | 75 | 2.91 | 24.21 | 75.7 | 0.85 | 11.76 | 1.23 | 44.94 | 14.33 | 20.17 |
| 8 | 105 | 2.77 | 26.25 | 73.7 | 1.52 | 12.12 | 2.30 | 41.42 | 17.80 | 18.63 |
| 9 | 165 | 2.91 | 61.93 | 38.0 | 0.98 | 11.49 | 1.03 | 44.61 | 14.71 | 20.39 |

C. S. = Carbon Selectivity
Carbon Selectivity as used herein with respect to a given product is the percent of carbon atoms in the total listed products present in the given product.

TABLE 6

| EXAMPLE | TIME MINS. | METHANOL WHSV Hr.-1 | UNREACTED METHANOL C. S. % | CONVERSION % | $CH_4$ C. S. % | $C_2H_4$ C. S. % | $C_2H_6$ C. S. % | $C_3H_6$ C. S. % | $C_3H_8$ C. S. % | $C_4$s C. S. % |
|---|---|---|---|---|---|---|---|---|---|---|
| 10 | 15 | 0.53 | 20.30 | 79.4 | 1.62 | 7.27 | 0.46 | 15.04 | 34.57 | 30.78 |
| 11 | 45 | 1.06 | 16.52 | 83.5 | 1.02 | 6.82 | 0.55 | 19.71 | 33.68 | 28.67 |
| 12 | 75 | 0.92 | 12.63 | 87.3 | 1.40 | 7.36 | 0.85 | 25.66 | 32.56 | 24.13 |
| 13 | 105 | 1.06 | 12.32 | 87.6 | 1.26 | 9.34 | 0.51 | 37.38 | 22.59 | 21.68 |
| 14 | 135 | 1.06 | 15.87 | 84.0 | 0.94 | 9.26 | 0.52 | 39.59 | 20.64 | 21.79 |
| 15 | 165 | 0.92 | 14.94 | 85.0 | 1.43 | 9.39 | 0.96 | 37.03 | 23.78 | 20.55 |
| 16 | 195 | 1.06 | 23.21 | 76.7 | 2.21 | 14.47 | 0.78 | 40.71 | 20.13 | 16.27 |

C. S. = Carbon Selectivity
Carbon Selectivity as used herein with respect to a given product is the percent of carbon atoms in the total listed products present in the given product.

Examples 6 to 9, when compared with Examples 10 to 16, illustrate certain advantages of using quinoline in the liquid of the slurry. In general, high selectivities to desired products, i.e., ethylene and propylene, are achieved at a given methanol conversion level if quinoline is present in the slurry. Thus, the quinoline in the slurry modifies the catalytic properties of the solid particles from Example 4. Since the catalyst binder and filler are known to promote non-selective reactions, the quinoline may act to reduce this undesirable effect. These non-selective reactions catalyzed by the catalyst binder and filler can be eliminated by eliminating the binder and filler from the catalyst. The present slurry reaction system is amenable to the use of sieving catalysts with no binders or fillers. Improved selectivities to desired products can be obtained. In addition, the present slurry system provides outstanding temperature control, and ease of catalyst handling and catalyst/product separation. In short, the present system provides substantial advantages over fixed catalyst beds, e.g., in temperature control and control in general, and over fluidized catalyst beds, e.g., in catalyst composition flexibility and reduced catalyst handling problems.

EXAMPLES 17 TO 22

Examples 6 to 9 were repeated except that 10 grams of catalyst were employed, the temperature within the autoclave was maintained at about 400° C. to about 410° C. and the pressure was maintained at 315 psig. Results of certain analyses, taken at various times, are shown in Table 7.

None of the products included more than 0.15% by weight of dimethyl ether.

TABLE 7

| EXAMPLE | TIME MINS. | METHANOL WHSV Hr.-1 | UNREACTED METHANOL C. S. % | CONVERSION % | $CH_4$ C. S. % | $C_2H_4$ C. S. % | $C_2H_6$ C. S. % | $C_3H_6$ C. S. % | $C_3H_8$ C. S. % | $C_4$s C. S. % |
|---|---|---|---|---|---|---|---|---|---|---|
| 17 | 195 | 1.64 | 16.20 | 83.8 | 1.64 | 19.12 | 2.21 | 50.79 | 7.81 | 13.81 |
| 18 | 225 | 1.45 | 19.53 | 80.8 | 1.20 | 19.18 | 1.69 | 51.68 | 7.09 | 14.36 |
| 19 | 315 | 1.45 | 9.16 | 90.7 | 1.65 | 21.32 | 2.05 | 51.32 | 6.64 | 12.77 |
| 20 | 345 | 1.45 | 10.82 | 89.1 | 1.65 | 20.99 | 2.12 | 50.96 | 6.78 | 13.12 |
| 21 | 375 | 1.52 | 12.46 | 87.5 | 1.66 | 20.95 | 2.34 | 50.61 | 6.65 | 13.35 |
| 22 | 405 | 1.45 | 11.53 | 88.4 | 1.73 | 21.08 | 2.34 | 50.51 | 6.86 | 13.12 |

C. S. = Carbon Selectivity
Carbon Selectivity as used herein with respect to a given product is the percent of carbon atoms in the total listed products present in the given product.

*Note: the WHSV values for rows 17–22 are 1.52, 1.45, 1.45, 1.45, 1.52, 1.45 respectively.*

EXAMPLE 23

This example illustrates the use of the present slurry system to convert methanol to gasoline boiling range hydrocarbons.

A slurry of 210 milliliters of Marlotherm S and 20 grams of solid particles, average size about 50 microns, comprising a crystalline aluminosilicate having a substantially uniform pore range of about 6 angstroms was placed in a 300 milliliter autoclave. The slurry was continuously agitated to keep the solid particles suspended in the Marlotherm S.

The autoclave was pressurized to 300 psig with nitrogen, and a nitrogen purge was established. The slurry was then heated to about 375° C. with electric heaters associated with the autoclave. When the temperature reached 375° C., a mixture of 50 vol. percent methanol and 50 vol. percent water was fed at the rate of 60 milliliters per hour until a total of 100 milliliters of this methanol/water mixture was fed.

All the products left the autoclave as a gas. After partial condensation of the products, a gas flow comprised largely of benzene and hydrogen (not counting the purge nitrogen) remained. The condensed liquid comprises water and gasoline boiling range hydrocarbons.

While the present invention was been described with respect to various specific examples and embodiments, it is to be understood that the invention is not limited thereto and that it can be variously practiced within the scope of the following claims.

What is claimed is:

1. A process for catalytically converting a feedstock into a product comprising contacting said feedstock with crystalline microporous three dimensional solid catalyst having the ability to promote said conversion at conditions effective to convert said feedstock to said product, said catalyst being present in a slurry with a liquid other than said feedstock or said product which is less reactive than said feedstock, wherein said liquid includes molecules having a kinetic diameter of a size to substantially prevent said liquid from entering the micropores of said catalyst.

2. The process of claim 1 wherein said feedstock is more soluble than said product in said liquid at said conditions.

3. The process of claim 2 wherein said product is substantially insoluble in said liquid at said conditions.

4. The process of claim 1 wherein said liquid includes at least one component effective to improve at least one property of said catalyst.

5. The process of claim 4 wherein said component is effective to improve the selectivity of said catalyst.

6. The process of claim 4 wherein said component is a base the molecules of which are substantially prevented from entering the pores of said catalyst.

7. The process of claim 4 wherein said component is a base which is selected from the group consisting of pyridine, pyridine derivatives, quinoline, quinoline derivatives and mixtures thereof.

8. The process of claim 1 wherein said feedstock is in the supercritical state at said conditions.

9. The process of claim 1 wherein said catalyst is included in solid particles containing no more than about 35% by weight of other solid material.

10. The process of claim 1 wherein said catalyst is included in solid particles containing substantially no other solid material.

11. The process of claim 1 wherein said catalyst is included in solid particles having improved smoothness relative to solid particles of similar composition obtained by mechanical size reduction.

12. The process of claim 1 wherein said catalyst is included in solid particles which have been spray dried.

13. The process of claim 1 wherein said catalyst is at least periodically contacted with regeneration medium to substantially maintain or improve the effectiveness of said catalyst to promote said conversion.

14. The process of claim 13 wherein said at least periodic contacting is conducted while said catalyst is in said slurry.

15. The process of claim 13 wherein said regeneration medium acts to reduce the average kinetic diameter of molecules present in the pores of said catalyst.

16. The process of claim 13 wherein said regeneration medium is a reducing medium or an oxidizing medium.

17. The process of claim 16 wherein said reducing medium is selected from the group consisting of hydrogen, carbon monoxide and mixtures thereof.

18. The process of claim 13 wherein said catalyst includes at least one added component effective to promote the action of said regeneration medium.

19. The process of claim 18 wherein said added component is a metal component.

20. The process of claim 18 wherein said regeneration medium is hydrogen and said component is effective to promote hydrogenation of molecules present in the pores of said catalyst at the conditions of said at least periodic contacting.

21. The process of claim 1 wherein said liquid is substantially non-reactive.

22. The process of claim 1 wherein said liquid is organic.

23. The process of claim 1 wherein said liquid includes carbon, hydrogen and at least one other element.

24. The process of claim 1 wherein said liquid is selected from the groups consisting of dibenzyl benzenes, diphenyl ether and mixtures thereof.

25. The process of claim 1 wherein said feedstock is organic.

26. The process of claim 25 wherein said feedstock contains 1 to about 10 carbon atoms per molecule.

27. The process of claim 25 wherein said feedstock contains 1 to about 4 carbon atoms per molecule.

28. The process of claim 25 wherein said feedstock includes carbon and hydrogen.

29. The process of claim 25 wherein said feedstock includes carbon, hydrogen and at least one other element.

30. The process of claim 25 wherein said feedstock comprises at least one aliphatic hetero compound.

31. The process of claim 25 wherein said feedstock is selected from the group consisting of methanol, ethanol, dimethyl ether, diethyl ether and mixtures thereof.

32. The process of claim 25 wherein said feedstock is methanol.

33. The process of claim 1 wherein said product is organic.

34. The process of claim 33 wherein said product contains 1 to about 10 carbon atoms per molecule.

35. The process of claim 33 wherein said product contains 2 to about 6 carbon atoms per molecule.

36. The process of claim 33 wherein said product includes carbon and hydrogen.

37. The process of claim 35 wherein said product is at least one light olefin.

38. The process of claim 1 wherein said contacting occurs in the presence of at least one diluent.

39. The process of claim 38 wherein said diluent includes molecules having a suitable kinetic diameter to allow said diluent to enter the pores of said catalyst.

40. The process of claim 38 wherein said feedstock and said diluent are both substantially continuously fed to said contacting.

41. The process of claim 38 wherein said feedstock and said diluent are combined prior to said contacting.

42. The process of claim 38 wherein said diluent comprises water.

43. The process of claim 1 wherein said catalyst is selected from the group consisting of layered clays, zeolitic molecular sieves, non-zeolitic molecular sieves and mixtures thereof.

44. The process of claim 1 wherein said catalyst is selected from the group consisting of non-zeolitic molecular sieves and mixtures thereof.

45. The process of claim 1 wherein said catalyst has a substantially uniform pore size.

46. The process of claim 1 wherein said catalyst is selected from the group consisting of silicoaluminophosphates and mixtures thereof.

47. The process of claim 44 wherein said catalyst is selected from the group consisting of SAPO-34, SAPO-17 and mixtures thereof.

48. The process of claim 44 wherein said catalyst is SAPO-34.

* * * * *